United States Patent [19]

Wagner et al.

[11] 4,060,455

[45] Nov. 29, 1977

[54] PROCESS FOR THE MICROBIAL PRODUCTION OF L-SERINE USING PSEUDOMONAS SP. DSM 672

[75] Inventors: Fritz Wagner, Braunschweig-Stockheim; Hermann Sahm, Wolfenbuttel; Walter Hartmut Keune, Braunschweig, all of Germany

[73] Assignee: Gesellschaft fur Biotechnologische Forschung mbH, (GBF), Braunschweig-Stockheim, Germany

[21] Appl. No.: 747,725

[22] Filed: Dec. 6, 1976

[30] Foreign Application Priority Data

Dec. 4, 1975 Germany ............................ 2554530

[51] Int. Cl.[2] ............................................ C12D 13/06

[52] U.S. Cl. ......................................... 195/29; 195/49

[58] Field of Search ...................... 195/29, 49, 96, 47, 195/79, 76, 112, 28 R, 30

[56] References Cited

U.S. PATENT DOCUMENTS

| | | | |
|---|---|---|---|
| 3,623,952 | 11/1971 | Kubota et al. | 195/29 |
| 3,692,628 | 9/1972 | Wakayama et al. | 195/28 R |
| 3,843,441 | 10/1974 | Kubota et al. | 195/30 |
| 3,880,741 | 4/1975 | Kageyama et al. | 195/29 |
| 3,939,042 | 2/1976 | Wakayama et al. | 195/49 |

OTHER PUBLICATIONS

Kubo et al., "L-Serine," *Chemical Abstracts,* vol. 82, No. 23, p. 410, (1975), abs. No. 153767y.

Wada, "L-Serine," *Chemical Abstracts,* vol. 68, No. 7, p. 2745, (1968), abs. No. 28476n.

Kubota et al., "Fermentative Production of L-Serine," *Chemical Abstracts,* vol. 75, No. 8, (1971), abs. No. 33893v.

Nakayama et al., "L-Serine," *Chemical Abstracts,* vol. 72, No. 7, (1970), pp. 183 and 184, abs. No. 30313h.

*Primary Examiner*—Raymond N. Jones
*Assistant Examiner*—Thomas G. Wiseman
*Attorney, Agent, or Firm*—Scully, Scott, Murphy & Presser

[57] ABSTRACT

L-serine is produced by aerobic cultivation of Pseudomonas Sp. DSM 672, or mutants thereof, in a nutrient medium including methanol and glycine.

14 Claims, No Drawings

PROCESS FOR THE MICROBIAL PRODUCTION OF L-SERINE USING PSEUDOMONAS SP. DSM 672

This invention relates to the production of L-serine from glycine and methanol in the presence of a submerse culture containing the bacterium Pseudomonas sp. DSM 672 and/or mutants thereof.

L-serine is an amino acid, which is used as a food additive, in the pharmaceutical industry and in the cosmetics industry. L-serine is also a starting substance for the production of other valuable compounds, for example, methyl serine. L-serine may also be of importance in the manufacture of synthetic fibres, since optically active serine as well as L-alanine and glycine, is a main constituent of natural silk.

L-serine has been produced by several methods. It may be obtained by the synthetic production of DL-serine which is then separated into the corresponding optical isomers for recovering L-serine.

Japanese Patent Specification No. 17 728/67 discloses a microbial process for the production of L-serine, in which DL-glycolic acid is added in addition to the carbon and energy source.

A microbiological process for the production of L-serine is disclosed in German Patent Specification No. 1 916 421, which uses carbohydrates or hydrocarbons as substrates. The microorganisms used in this process require isoleucine for growth purposes.

A process is also known in which glycine, a preliminary stage of serine in the metabolism, is microbially reacted to L-serine (J. Agric. Chem. Soc. Jap., 48 (2), 125 - 129, (1974)). Glucose is preferably used as carbon and energy source according to this microbial process.

The object of the process according to the invention is to avoid the disadvantages arising from the use of a costly carbon and energy source of the known processes, which is technically undesirable as regards fermentation.

Therefore according to the present invention there is provided a process for the production of L-serine in which methanol and glycine are mixed with a submerse culture containing inorganic nutrients and the bacterium Pseudomonas sp. DSM 672 and/or mutants of this bacterium in a reactor supplied with a gas which is air or oxygen-enriched air at a pH in the range 80 to 90 and at a temperature in the range 20° to 40° C, the mixture is allowed to react, the resulting cell mass is separated from the culture filtrate and the L-serine is isolated from the culture filtrate.

The invention provides a new process for the production of L-serine starting from glycine and methanol using certain microorganisms. The L-serine produced in the culture filtrate may be isolated by techniques known in the art.

The submerse culture is preferably cultivated in a reactor supplied with air or oxygen-enriched air by providing inorganic nutrients, the bacterium Pseudomonas sp DSM 672 and/or mutants thereof, at a reaction temperature of 20° to 40° C at a pH in the range 6.5 to 8.0 with a methanol concentration of from 0.1 to 1.0% by volume as carbon and energy source to facilitate multiplication of the bacterium. The cultivation may be effected continuously in a first reactor and a portion of the culture transferred to second reactor for the production of L-serine of the cultivation and L-serine production may be effected in a single reactor.

The glycine is preferably added to the submersed culture in an amount to give an initial concentration of 0.5 to 2.0% by weight and methanol is added to maintain a constant value in the the range 0.5 to 2.0% by weight. The temperature of the reactor is preferably maintained at 28° to 33° C and the contents may be mixed with a mechanical stirrer and/or by aeration with the gas.

After the formation of L-serine the cell mass is separated from the culture filtrate and the L-serine isolated. The L-serine free culture filtrate may be wholly or partially returned to the reactor or discarded.

In one embodiment of the invention the L-serine production by the bacterium is effected with addition of surface-active substances or substances which influence the cell wall for the purpose of improving the permeability. A preferred surface-active substance is lauryl sulphate.

Urea and/or $NH_4$ or $NO_3$ salts may also be included as nitrogen source.

The bacterium used in the invention, for the production of L-serine, the microorganism Pseudomonas sp. DMS 672, which microorganism has been isolated from a soil sample. Mutants such as the strain DSM 673, may also be employed.

The bacterium Pseudomonas sp. DSM 672 has been filed in the German Collection of Microorganisms in Gottimgem under the number DSM 672 and the mutant under the number DSM 673.

The bacterium Pseudomonas sp. DSM 672 is characterised by the following properties:

Cell morphology:

bacillus, mobile within limits, with a polar flagellum.

Colony morphology:

strong pink colour, round and smooth, about 0.5 - 2 mm diameter after 3 - 4 days Strain property:

gram-negative, cell dry mass a strong pink colour

Physiology:

strictly aerobic, methanol-dehydrogenanse positive, hydroxypyruvate-reductase positive, hexosephosphate synthetase negative Growth properties:

| | Minimum | Optinum | Maximum |
|---|---|---|---|
| temperature (° C) | 5–10 | 28–33 | 37 |
| pH | 6.0 | 7–8 | 9.0 |
| methanol conc. % (V/V) | 0.2 | 0.5–1.5 | 4.0 |

Pseudomonas sp. DSM 672 is able to grow on methanol and on certain organic acids, such as succinate, pyruvate and malate, as carbon and energy source, but not on methane, methylamine, ethanol, acetate or glucose.

The process of the invention can also be carried out with mutants of the Pseudomonas sp DSM 672 strain, which are distinguished from the "wild" type in that they are no longer able, without addition of glycine, to grow on succinate as single carbon and energy source. Such mutants can be obtained with the aid of chemical and physical methods. These mutants also have the L-serine accumulation capacity of the initial strain. Included in the measures by which the mutants can be produced are, for example, X-rays and ultra-violet rays, treatments with nitrogen-mustard gases or organic peroxides.

The invention will now be illustrated by the following Examples.

EXAMPLE 1

An agar slanting tube culture of Pseudomonas sp. DSM 672 on a defined medium was introduced into 100 ml of a liquid medium in a flask, which was sterilised beforehand for 20 minutes at 120° C and to which then 1% of methanol was added under aseptic conditions.

The medium contained the following nutrients: 0.10 g of $KH_2PO_4$, 0.45 g of $Na_2HPO_4$, 0.20 g of $(NH_4)_2SO_4$, 0.04 g of $MgSO_4.7H_2O$, 2.0 mg of $CaCl_2.2H_2O$, 1.0 mg of $FeSO_4.7H_2O$, 0.5 mg of $MnSO_4.H_2O$, 0.1 mg of $(NH_4)_2Mo_7O_{24}$. $7H_2O$ and 1 ml of methanol to 100 ml of distilled water. The culture was aerobically incubated for 40 hours at 30° C on a rotary shaker machine. 1% of this grown culture served as inoculum for a liquid culture having the same composition as the medium and the same incubation conditions, apart from the uncubation time. During the incubation, altogether another 1% of methanol was twice added, at intervals from 15 to 20 hours. Before each addition, the pH value of the submerse culture was adjusted with 1N-NaOH to 7.0 After a multiplication phase of 45 to 60 hours, the pH value was adjusted to 8.5 with 1N-NaOH, and again 2% (V/V) of methanol and simultaneously 2% (W/V) of glycine were added. After another 30 to 50 hours, 4 g/l of L-serine were detected in the nutrient medium.

EXAMPLE 2

A reactor, filled with 10 liters of nutrient solution of the same composition as in Example 1 was sterilised for 10 minutes at 121° C, cooled to 30° C, 0.5% (V/V) of methanol added aseptically and inoculated with 200 ml of inoculum of Pseudomonas sp. DSM 672, prepared as in Example 1. The submerse culture was cultivated at 30° C and with use of a blade-type stirrer with an aeration rate of 600 l/h/total batch. In the first phase of the growth or cultivation, the methanol concentration was automatically held constant at 0.5% by volume, and in addition, a pH value of 7.0 was automatically maintained with a pH control station by addition of a 12% by volume ammonia solution. After 40 to 60 hours, the pH value was adjusted to 8.5 and maintained at this value until the growing process was halted. The methanol concentration was raised to 2% and kept constant at this value and at the same time 2% of glycine were added and the aeration rate reduced to 200 l/h/total batch. After a process lasting 80 to 100 hours, the L-serine concentration in the nutrient solution amounted to 5 to 6 g/l.

EXAMPLE 3

The process was carried out in accordance with Example 2, using the mutant DSM 673 in place of the Pseudomonas sp. DSM 672 strain. The yield of L-serine in the nutrient medium amounted to 8 to 10 g/l, under the practically identical processing conditions.

What we claim is:

1. A process for the production of L-serine in which methanol and glycine are mixed with a submerse culture containing inorganic nutrients and the bacterium Pseudomonas sp. DSM 672 and/or L-Serine accumulating mutants of this bacterium in a reactor supplied with a gas which is air or oxygen-enriched air at a pH in the range 6.0 to 9.0 and at a temperature in the range 20° to 40° C, the mixture is allowed to react, the resulting cell mass is separated from the culture filtrate and the L-serine is isolated from the culture filtrate.

2. A process as claimed in claim 1 in which strain DSM 673 is used as mutant.

3. A process as claimed in claim 1 in which the initial glycine concentration is 0.5 to 2.0% by weight.

4. A process as claimed in claim 3 in which the methanol concentration is maintained at a constant value in the range 0.5 to 2.0% by volume.

5. A process as claimed in claim 1 in which the contents of the reactor are stirred mechanically.

6. A process as claimed in claim 1 in which the contents of the reactor are stirred by the introduction of the gas.

7. A process as claimed in claim 1 in which the reactor temperature is in the range 28° to 33° C.

8. A process as claimed in claim 1 in which the submerse culture is cultivated in a reactor supplied with air or oxygen-enriched air by providing inorganic nutrients, the bacterium Pseudomonas sp DSM 672 and/or mutants thereof, at a reaction temperature of 20° to 40° C and at a pH in the range 6.5 to 8.0 with a methanol concentration of from 0.1 to 1.0% by volume as carbon and energy source to facilitate multiplication of the bacterium.

9. A process as claimed in claim 8 in which the cultivation of the submerse culture containing the bacterium Pseudomonas and/or mutants thereof is effected continuously in a first reactor and a portion of the submerse culture is transferred into a second reactor for the production of L-serine.

10. A process as claimed in claim 8 in which the cultivation of the submerse culture and production of L-serine is effected in a single reactor.

11. A process as claimed in claim 8 in which the production of L-serine is effected in the presence of a surface-active substance which influences the cell wall to improve the permeability.

12. A process as claimed in claim 11 in which the surface-active substance is lauryl sulphate.

13. A process as claimed in claim 8 in which urea and/or $NH_4$ or $NO_3$ salts are introduced as a nitrogen source.

14. A process as claimed in claim 1 in which at least a portion of the culture filtrate from which the L-serine is isolated is returned to the reactor.

* * * * *